United States Patent [19]

Meyer et al.

[11] 4,404,391
[45] Sep. 13, 1983

[54] METHOD FOR THE PREPARATION OF N-METHYL AND -N-ETHYL-1-PYRROLIDONES

[75] Inventors: Peter J. N. Meyer, Munstergeleen; Josef M. Penders, Maastricht, both of Netherlands

[73] Assignee: Stamicarbon B.V., Geleen, Netherlands

[21] Appl. No.: 249,983

[22] Filed: Apr. 1, 1981

[30] Foreign Application Priority Data

Apr. 4, 1980 [NL] Netherlands .......................... 8002019

[51] Int. Cl.³ ................. C07D 207/267; C07D 207/27
[52] U.S. Cl. .................................................. 548/552
[58] Field of Search .............. 260/326.5 FL; 546/243, 546/158; 548/552

[56] References Cited

U.S. PATENT DOCUMENTS 3,073,843  11/1963  Buc ........................... 260/326.5 FL
3,274,211   9/1966  Schmerling ..................... 546/243
3,821,245   6/1974  Kanetaka et al. .................. 548/552

FOREIGN PATENT DOCUMENTS 2135211  7/1971  Fed. Rep. of Germany ... 260/326.5 FL
1027949  5/1966  United Kingdom ...... 260/326.5 FL

OTHER PUBLICATIONS

Auerbach et al., J. Org. Chem., vol. 41, No. 4, 1976, pp. 725 & 726.
Brennstoff-Chemie, Nr. 5 Bd. 48, pp. 135–139.
Merck Chemical Index, p. 897, (8th Ed. 1968).
Harrison & Harrison, vol. 1, Comp. of Synthetic Methods, pp. 211–212, (1971).
Bernardi et al., J. Chem. Soc. Chem. Comm. 320, (1975).
Johnson and Crosby, J. Org. Chem. 27, 2205, (1962).
Basha et al., Synthetic Communications 7(8), pp. 549–552, (1977).
J. March, Advanced Organic Chemistry, pp. 388–389, (1977).
Kirk–Othmer, Encyclopedia of Chem. Tech., vol. 19, pp. 514, 517–520, (3rd Ed., 1982).

Primary Examiner—Mark L. Berch
Assistant Examiner—D. B. Springer

[57] ABSTRACT

The invention relates to a process for the preparation of a N-alkyl-2-pyrrolidone by reducing the corresponding N-($\alpha$-hydroxyalkyl)-2-pyrrolidone in the liquid phase under an atmosphere of hydrogen gas and in the presence of a noble metal hydrogenation catalyst while in the absence of trifluoroacetic acid.

7 Claims, No Drawings

METHOD FOR THE PREPARATION OF N-METHYL AND -N-ETHYL-1-PYRROLIDONES

The invention relates to a process for the preparation of N-alkyl-2-pyrrolidones by reducing the corresponding N-(α-hydroxyalkyl)-2-pyrrolidones.

Two methods for reducing an N-hydroxymethylpyrrolidones to the corresponding N-methylpyrrolidone are described in *Journal of Organic Chemistry*, Volume 41, No. 4, pages 725–726 (1976). In the first method, the reduction is performed with triethylsilane in the presence of trifluoroacetic acid whereas the second reduction method uses hydrogen with a palladium on carbon hydrogenation catalyst in the presence of trifluoroacetic acid. The presence of trifluoroacetic acid probably causes the hydroxymethyl pyrrolidone to form an acyliminium ion which is reduced to the N-methylpyrrolidone.

A third reduction method described in Synthetic Communications 7 (8), 549–552 (1977) uses cyanoborohydride in trifluoroacetic acid.

These already known methods suffer from several disadvantages. The required presence of trifluoroacetic acid is the major difficulty since the process equipment must then be constructed in practice from very costly materials to properly use and control said acid. In addition, the low yield of N-alkyl-2-pyrrolidone which is realized per gram of palladium on carbon hydrogenation catalyst, according to the disclosure in said Journal of Organic Chemistry-publication, results in high catalyst costs and the triethylsilane and cyanoborohydride reducing agents are not really suitable at all for practical applications.

It has now been found that reducing N-(α-hydroxyalkyl)-2-pyrrolidones to the corresponding N-alkyl-2-pyrrolidones can be achieved with lower reductant costs.

According to the present invention, the preparation of N-alkyl-2-pyrrolidones by reduction of the corresponding N-(α-hydroxyalkyl)-2-pyrrolidones is carried out in the liquid phase with hydrogen and a hydrogenation catalyst, and in the absence of trifluoroacetic acid.

N-hydroxymethyl-2-pyrrolidone and N-(α-hydroxyethyl)-2-pyrrolidone are suitable starting products. The pyrrolidone ring may be substituted, for example, with one or more lower alkyl groups of from 1 to 4 C atoms. The N-hydroxymethyl-2-pyrrolidones can be obtained according to the process described in U.S. Pat. No. 3,073,843, wherein formaldehyde is reacted with the pyrrolidone in the presence of a strong alkaline compound as catalyst, such as potassium hydroxide. For example, N-(α-hydroxyethyl)-2-pyrrolidones can be prepared according to Brennstoff-Chemie Nr. 5 Bd. 48, pages 136–139, by reacting acetaldehyde with the relative, i.e. corresponding, 2-pyrrolidone in the presence of an acid catalyst such as anhydrous hydrogen chloride.

In the process according to the present invention, various already known noble metal hydrogenation catalysts can be used including platinum, ruthenium and palladium, on suitable carriers such as carbon, aluminium oxide or silicon oxide. Palladium on carbon is the preferred catalyst since the starting material is rapidly reduced.

According to the present invention, the reduction can be easily performed in a solvent or a distributing agent. In principle any inert solvent or distributing agent is suitable. The N-alkyl-2-pyrrolidone corresponding to the product being prepared can also be used as the reaction solvent. Preferably the reduction is carried out in water.

The reduction can be carried out at different temperatures, for example, between room temperature (e.g. 20° C.) and 150° C. Temperatures between about 50° and 125° C. are preferred.

The partial hydrogen pressure may vary, for example, between 1 and 175 bar. In principle pressures in excess of 175 bar can also be applied but do not result in any advantage. In practice, favorable results can be achieved at partial hydrogen pressures of between 25 and 125 bar.

The process according to the present invention may be carried out continuously or discontinously in different ways, for example, in a stirred reactor system, a loop reactor or a trickle phase reactor.

According to the present invention, in the preparation of N-methyl-2-pyrrolidone from a hydroxymethyl pyrrolidone prepared by the addition of formaldehyde to the corresponding 2 pyrrolidone using catalytic quantities of a strong alkali, the resultant reaction mixture is a suitable starting material without further purification.

The solvent or the distributing agent, for example water, may, if desired, already be present when adding the formaldehyde to the relative pyrrolidone.

In performing the reduction according to the present invention, the resultant reaction mixture can be worked up by known methods, such as distillation, while recovering the desired product and possibly non-converted starting compound.

The products prepared according to the present invention can be used as solvents for polyurethanes for example, and as selective extracting agents in the petroleum industry.

The process according to the invention is illustrated further in the following non-limiting examples.

EXAMPLE I

A 2 liter autoclave, having a stirrer and a heating jacket, is filled with 1000 g of water, 32 g of palladium on carbon catalyst (5% by weight of Pd) and 100 g of unpurified N-hydroxymethylpyrrolidone (prepared from 73.8 g of pyrrolidone, 26 g of paraformaldehyde and 0.2 g KOH in the manner as described in U.S. Pat. No. 3,073,843). After closing, the autoclave is flushed with nitrogen. Subsequently, the autoclave is filled with hydrogen to a pressure of 100 bar, and then while stirring vigorously, the mixture in the autoclave is heated to 100° C. The hydrogen pressure is then about 110 bar. At this temperature, the stirring is continued until no more hydrogen is taken up. This takes about 30 minutes. After rapid cooling, the gas-chromatographical analysis of the resultant reaction mixture showed a 96% conversion of N-hydroxymethylpyrrolidone to N-methylpyrrolidone and a yield of 95% of the theoretical possible yield.

EXAMPLE II

Example I is repeated, however the starting product is purified by recrystallization from toluene. 24 g of the palladium on carbon catalyst are used. 1000 g of N-methylpyrrolidone replaced the 1000 g of water used in Example 1 as the distributing agent. It now takes 90 minutes to complete the hydrogen take-up. The conversion was 94% and the yield corresponds to 87% of the theoretical yield.

EXAMPLE III

An autoclave as described in Example I is filled with 500 g of formaline (37% formaldehyde by weight) and a mixture of 524 g pyrrolidone and 29 g of potassium carbonate. The autoclave is closed, flushed with nitrogen and subsequently, while stirring, heated for 2 hours at 80° C. 124 g of palladium on carbon catalyst (2% by weight of Pd) is then pressed into the autoclave through a dosing vessel. Hydrogen is added until the pressure reaches 100 bar. While stirring, the reaction mixture is kept at a temperature of 80° C. for 120 minutes. At this point no more hydrogen is taken up. After cooling, analysis of the reaction mixture showed that 415.5 g of N-methylpyrrolidone was obtained. The pyrrolidone conversion amounts to 90%. 75.6% of the converted pyrrolidone was converted into the desired product.

EXAMPLE IV

An autoclave as in Example I is filled with 1000 g of water, 26 g of palladium on carbon catalyst (2% by weight of Pd) and 100 g of N (α-hydroxyethyl)-pyrrolidone. The autoclave is closed and flushed with nitrogen. Hydrogen is then pressed into the autoclave to a pressure of 50 bar, and the mixture is heated up to 100° C. while stirring vigorously. While stirring continues, the mixture in the autoclave is kept at 100° C. for 60 minutes. By this time hydrogen take-up has stopped. After cooling, the resultant reaction mixture analysis showed complete starting product conversion and a yield corresponding to 99.2% of the theoretically possible N-ethylpyrrolidone yield.

What is claimed is:

1. A process for the preparation of N-methyl-2-pyrrolidone or N-ethyl-2-pyrrolidone which consists essentially in the step of reducing the corresponding N-(α-hydroxyalkyl)-2-pyrrolidone in the liquid phase in a trifluoroacetic acid free inert solvent selected from the group consisting of water, N-methyl-2-pyrrolidone, or N-ethyl-2-pyrrolidone under an atmosphere of hydrogen gas at a partial hydrogen pressure of between 1 bar and 175 bar at a temperature of between 20° C. and 150° C. in the presence of a noble metal hydrogenation catalyst wherein the metal component thereof is selected from the group consisting of platinum, ruthenium, and palladium.

2. Process according to claim 1 wherein said hydrogenation catalyst is palladium on carbon.

3. Process according to either claim 1 or 2, wherein said reduction is carried out at a temperature between about 50° C. and 125° C.

4. Process according to either claim 1 or 2, wherein the partial hydrogen pressure is from 25 bar to 125 bar.

5. Process according to either claim 1 or 2 wherein said N-methyl-2-pyrrolidone is obtained by subjecting an unpurified reaction mixture to said reduction, said reaction mixture being obtained by the addition of formaldehyde and the corresponding 2-pyrrolidone in the presence of a catalytic quantity of strong alkali.

6. Process according to claim 1 wherein said N-(α-hydroxyalkyl)-2-pyrrolidone has at least one 1 to 4 carbon atom alkyl group substituent on the pyrrolidone ring.

7. A process for the preparation of N-methyl-2-pyrrolidone or N-ethyl-2-pyrrolidone which consists essentially in reducing the corresponding N-(α-hydroxyalkyl)-2-pyrrolidone in the liquid phase in a trifluoroacetic acid free inert solvent selected from the group consisting of water, N-ethyl-2-pyrrolidone or N-methyl-2-pyrrolidone under hydrogen gas at a partial hydrogen pressure of between 25 bar and 125 bar at a temperature of between 50° C. and 125° C. in the presence of a noble metal hydrogenation catalyst wherein the metal component thereof is selected from the group consisting of: platinum, ruthenium and palladium.

* * * * *